US010786311B2

(12) United States Patent
Salazar et al.

(10) Patent No.: US 10,786,311 B2
(45) Date of Patent: Sep. 29, 2020

(54) APPARATUS AND METHOD FOR REGISTERING FACIAL LANDMARKS FOR SURGICAL NAVIGATION SYSTEM

(71) Applicant: Acclarent, Inc., Irvine, CA (US)

(72) Inventors: Henry F. Salazar, Pico Rivera, CA (US); Jetmir Palushi, Irvine, CA (US); Ehsan Shameli, Irvine, CA (US); George L. Matlock, Pleasanton, CA (US); Itzhak Fang, Jr., Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 279 days.

(21) Appl. No.: 15/852,169

(22) Filed: Dec. 22, 2017

(65) Prior Publication Data

US 2019/0192228 A1    Jun. 27, 2019

(51) Int. Cl.
A61B 34/20    (2016.01)
A61B 90/50    (2016.01)
(Continued)

(52) U.S. Cl.
CPC ............. *A61B 34/20* (2016.02); *A61B 17/24* (2013.01); *A61B 90/13* (2016.02); *A61B 90/50* (2016.02); *A61B 5/061* (2013.01); *A61B 2017/00725* (2013.01); *A61B 2017/246* (2013.01); *A61B 2034/2048* (2016.02); *A61B 2034/2051* (2016.02); *A61B 2034/2055* (2016.02); *A61B 2034/2063* (2016.02); *A61B 2034/2065* (2016.02); *A61B 2034/2068* (2016.02); *A61B 2034/2072* (2016.02); *A61B 2090/363* (2016.02); *A61B 2090/364* (2016.02); *A61B 2090/365* (2016.02); *A61B 2090/373* (2016.02);
(Continued)

(58) Field of Classification Search
CPC ......... A61B 90/13; A61B 90/50; A61B 17/24; A61B 34/20
See application file for complete search history.

(56) References Cited

U.S. PATENT DOCUMENTS 7,720,521 B2    5/2010  Chang et al.
8,320,711 B2   11/2012  Altmann et al.
(Continued)

FOREIGN PATENT DOCUMENTS

EP    2289597 A1    3/2011

OTHER PUBLICATIONS

U.S. Appl. No. 62/555,824, entitled "Apparatus to Secure Field Generating Device to Chair," filed Sep. 8, 2017.
(Continued)

*Primary Examiner* — Bryan Bui
(74) *Attorney, Agent, or Firm* — Frost Brown Todd LLC

(57) ABSTRACT

An array of sensors may be used to perform touchless registration of landmarks of a patient's face before an ENT procedure in order to associate those landmarks with pre-operative images in three-dimensional space, which is required for image guided surgery features such as navigation. Touchless or light-touch registration may improve accuracy by avoiding the need for substantial pressing against a patient's skin, which may deform and thereby introduce erroneous registration data. A sensor may also be implemented in forms other than an array such as handheld probe having a single sensor as opposed to an array.

19 Claims, 13 Drawing Sheets

(51) Int. Cl.
    *A61B 17/24*     (2006.01)
    *A61B 90/13*     (2016.01)
    *A61B 90/00*     (2016.01)
    *A61B 5/06*     (2006.01)
    *A61B 17/00*     (2006.01)

(52) U.S. Cl.
    CPC ............... *A61B 2090/3762* (2016.02); *A61B 2562/0257* (2013.01)

(56) References Cited

U.S. PATENT DOCUMENTS

| | | | |
|---|---|---|---|
| 8,702,626 | B1 | 4/2014 | Kim et al. |
| 10,362,965 | B2 * | 7/2019 | Kesten .................. A61B 5/055 |
| 2007/0126716 | A1 | 6/2007 | Haverly |
| 2008/0079421 | A1 | 4/2008 | Jensen |
| 2011/0004057 | A1 | 1/2011 | Goldfarb et al. |
| 2011/0060214 | A1 | 3/2011 | Makower |
| 2014/0364725 | A1 | 12/2014 | Makower |
| 2016/0008083 | A1 | 1/2016 | Kesten et al. |
| 2016/0310042 | A1 | 10/2016 | Kesten et al. |
| 2017/0119473 | A1 | 5/2017 | Clopp |

OTHER PUBLICATIONS

International Search Report and Written Opinion dated May 21, 2019 for International Application No. PCT/IB2018/060350, 10 pages.

\* cited by examiner

APPARATUS AND METHOD FOR REGISTERING FACIAL LANDMARKS FOR SURGICAL NAVIGATION SYSTEM

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

An example of an electromagnetic IGS systems that may be used in ENT and sinus surgery is the CARTO® 3 System by Biosense-Webster, Inc., of Irvine, Calif. When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result, IGS systems may be particularly useful during performance of FESS, balloon sinuplasty, and/or other ENT procedures where anatomical landmarks are not present or are difficult to visualize endoscopically.

One function that may be performed by an IGS system is obtaining a reference point that can be used to correlate various preoperatively obtained images with a patient's actual position during a procedure. This act may be referred to as patient registration. Patient registration is conventionally performed by using a positionally tracked instrument (e.g., a guidewire whose tip position may be detected in three-dimensional space) to trace the area of a patient that will be affected by the procedure. For example, in the case of a balloon sinuplasty or other ENT procedure, a positionally tracked guidewire or other tool may be used to trace or touch one or more positions on a patient's face. At each touch point, a positional tracking system will register that point in three-dimensional space and, using a number of registered points, determine the position of the affected area in three-dimensional space. Once the affected area is fully mapped or registered, it can be correlated with preoperative images in order to provide a seamless IGS experience across varying types of preoperative images during the performance of the procedure. Performing patient registration in this manner is both time consuming and error prone, due to the number of touch points required for some procedures and the relative inaccuracy of pressing a flexible guidewire tip against the non-rigid surface of a patient's face.

It may be desirable to provide features that further facilitate the use of an IGS navigation system and associated components in ENT procedures and other medical procedures. While several systems and methods have been made and used with respect to IGS and ENT surgery, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The inventors have conceived of novel technology that, for the purpose of illustration, is disclosed herein as applied in the context of image guided surgery. While the disclosed applications of the inventors' technology satisfy a long-felt but unmet need in the art of image guided surgery, it should be understood that the inventors' technology is not limited to being implemented in the precise manners set forth herein, but could be implemented in other manners without undue experimentation by those of ordinary skill in the art in light of this disclosure. Accordingly, the examples set forth herein should be understood as being illustrative only, and should not be treated as limiting.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY IMAGE GUIDED SURGERY NAVIGATION SYSTEM

Figure 1:
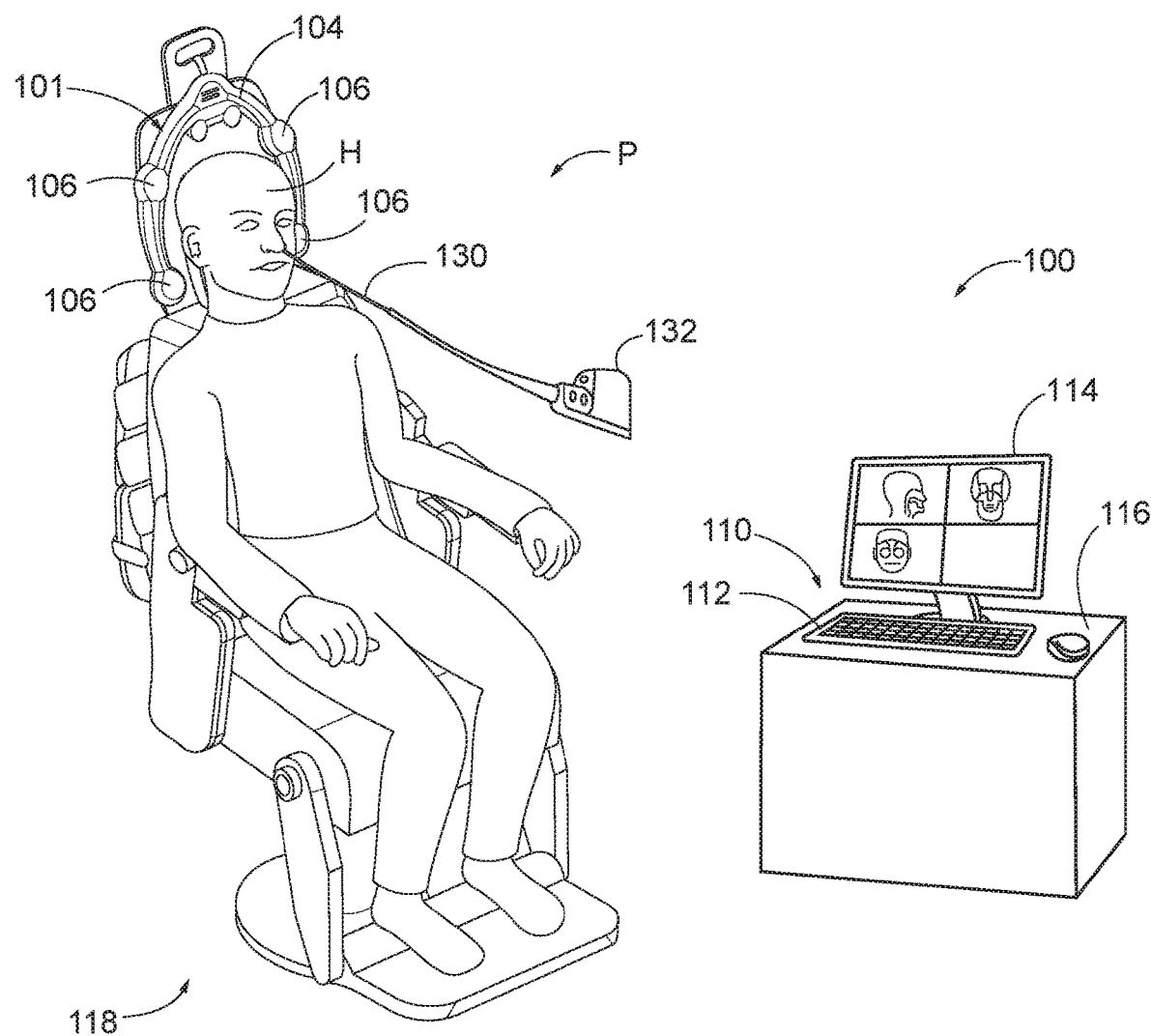
FIG. 1 depicts a schematic view of an exemplary sinus surgery navigation system being used on a patient seated in an exemplary medical procedure chair.

FIG. 1 shows an exemplary IGS navigation system (100) enabling an ENT procedure to be performed using image guidance. In some instances, IGS navigation system (100) is used during a procedure where dilation instrument assembly (10) is used to dilate the ostium of a paranasal sinus; or to dilate some other anatomical passageway (e.g., within the ear, nose, or throat, etc.). In addition to or in lieu of having the components and operability described herein IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 7,720,521, entitled "Methods and Devices for Performing Procedures within the Ear, Nose. Throat and Paranasal Sinuses," issued May 18, 2010, the disclosure of which is incorporated by reference herein; U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pub. No. 2016/0310042, entitled "System and Method to Map Structures of Nasal Cavity," published Oct. 27, 2016, issued as U.S. Pat. No. 10,362,965 on Jul. 30, 2019; and U.S. Pat. Pub. No. 2011/0060214, entitled "Systems and Methods for Performing Image Guided Procedures within the Ear, Nose, Throat and Paranasal Sinuses," published Mar. 10, 2011, issued as U.S. Pat. No. 10,241,399 on Mar. 26, 2019, the disclosure of which is incorporated by reference herein.

IGS navigation system (100) of the present example comprises a field generator assembly (101), which comprises set of magnetic field generators (106) that are integrated into a horseshoe-shaped frame (104). Field generators (106) are operable to generate alternating magnetic fields of different frequencies around the head of the patient. Field generators (106) thereby enable tracking of the position of a navigation guidewire (130) that is inserted into the head of the patient. Various suitable components that may be used to form and drive field generators (106) will be apparent to those of ordinary skill in the art in view of the teachings herein.

In the present example, frame (104) is mounted to a chair (118), with the patient (P) being seated in the chair (118) such that frame (104) is located adjacent to the head (H) of the patient (P). By way of example only, chair (118) and/or field generator assembly (101) may be configured and operable in accordance with at least some of the teachings of U.S. Patent App. No. 62/555,824, entitled "Apparatus to Secure Field Generating Device to Chair," filed Sep. 8, 2017, the disclosure of which is incorporated by reference herein.

IGS navigation system (100) of the present example further comprises a processor (110), which controls field generators (106) and other elements of IGS navigation system (100). For instance, processor (110) is operable to drive field generators (106) to generate electromagnetic fields; and process signals from navigation guidewire (130) to determine the location of a sensor in navigation guidewire (130) within the head (H) of the patient (P). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

A coupling unit (132) is secured to the proximal end of a navigation guidewire (130). Coupling unit (132) of this example is configured to provide wireless communication of data and other signals between console (116) and navigation guidewire (130). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Navigation guidewire (130) may be used as a substitute for guidewire (30) in dilation instrument (20) described above. Navigation guidewire (130) includes a sensor (not shown) that is responsive to movement within the fields generated by field generators (106). In the present example, the sensor of navigation guidewire (130) comprises at least one coil at the distal end of navigation guidewire (130). When such a coil is positioned within an electromagnetic field generated by field generators (106), movement of the coil within that magnetic field may generate electrical current in the coil, and this electrical current may be communicated along the electrical conduit(s) in navigation guidewire (130) and further to processor (110) via coupling unit (132). This phenomenon may enable IGS navigation system (100) to determine the location of the distal end of navigation guidewire (130) within a three-dimensional space (i.e., within the head (H) of the patient (P)). To accomplish this, processor (110) executes an algorithm to calculate location coordinates of the distal end of navigation guidewire (130) from the position related signals of the coil(s) in navigation guidewire (130).

Processor (110) uses software stored in a memory of processor (110) to calibrate and operate system (100). Such operation includes driving field generators (106), processing data from navigation guidewire (130), processing data from operating controls (112), and driving display screen (114). Processor (110) is further operable to provide video in real time via display screen (114), showing the position of the distal end of navigation guidewire (130) in relation to a video camera image of the patient's head (H), a CT scan image of the patient's head (H), and/or a computer generated three-dimensional model of the anatomy within and adjacent to the patient's nasal cavity. Display screen (114) may display such images simultaneously and/or superimposed on each other during the surgical procedure. Such displayed images may also include graphical representations of instruments that are inserted in the patient's head (H), such as navigation guidewire (130), such that the operator may view the virtual rendering of the instrument at its actual location in real time. By way of example only, display screen (114) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (114).

The images provided through display screen (114) may help guide the operator in maneuvering and otherwise manipulating instruments within the patient's head. When used as a substitute for guidewire (30) in dilation instrument assembly (10), navigation guidewire (130) may facilitate navigation of instrumentation of dilation instrument assembly (10) within the patient during performance of a procedure to dilate the ostium of a paranasal sinus; or to dilate some other anatomical passageway (e.g., within the ear, nose, or throat, etc.). It should also be understood that other components of dilation instrument assembly (10) may incorporate a sensor like the sensor of navigation guidewire (130), including but not limited to dilation catheter (40).

II. EXEMPLARY TOUCH INSTRUMENT TO REGISTER AND CALIBRATE IMAGE GUIDED SURGERY SYSTEM

As noted above, a variety of guidewires may be used to perform registration and calibration in an IGS navigation system (100) by touching various points on the patient's face with the positionally tracked guidewire tip. Such guidewires may be rather flimsy or flexible by their very nature. This flexibility may make it difficult for an operator to grasp the guidewire by itself and manipulate the distal tip of the guidewire to contact registration points on the patient's head. For instance, the distal tip of the guidewire may tend to deflect in response to engagement with the patient's head, which may compromise the accuracy of the registration. It may therefore be desirable to at least temporarily provide rigidity to a guidewire during the process of registration and calibration in an IGS navigation system (100). Such added rigidity may make it easier for the operator to handle the guidewire, may prevent the distal tip of the guidewire from deflecting in response to engagement with the patient's head, and may ultimately provide a more accurate registration.

Figure 2:
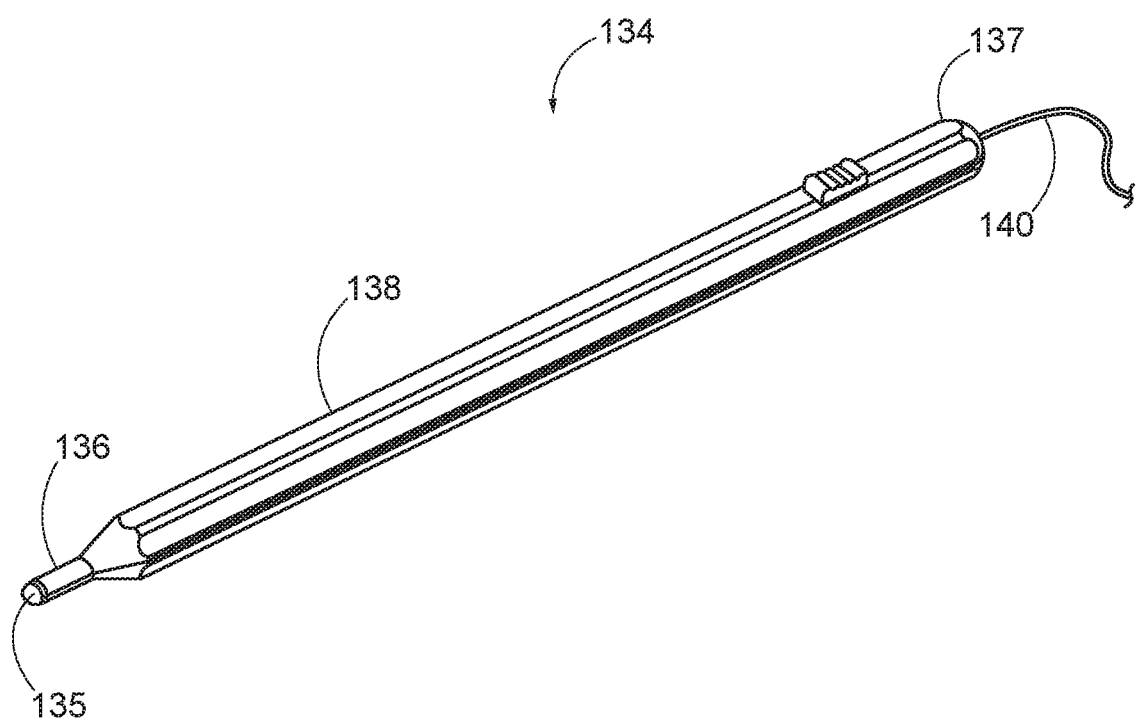
FIG. 2 is a front perspective view of an exemplary registration probe having a position sensing tip.

FIG. 2 show an exemplary touch based registration and calibration instrument (134) that may be used to temporarily provide rigidity to an otherwise flimsy guidewire in order to register and calibrate an IGS navigation system such as IGS navigation system (100) described above. Calibration instrument (134) of this example comprises a rigid elongate body (138) having a distal end (136) and a proximal end (137). In some versions, elongate body (138) is formed of a transparent polycarbonate material. Distal end (136) includes a taper leading to a reduced diameter portion, which ultimately terminates in a rounded distal tip (135).

A guidewire (140) may be inserted into the rigid elongate body (138) so that an end of the guidewire (140) rests against the interior of the rounded distal tip (135). Since end of the guidewire (140) is positionally tracked, the rounded distal tip (135) may be used to touch a registration point on a patient's face, which will place the positionally tracked tip within close proximity of the registration point, separated only by the known width of a wall of the rigid elongate body (138). In this configuration, instrument (134) may be used to perform the registration and calibration process associated with IGS navigation system (100) by touching the rounded distal tip (135) to each registration point while providing another input to the system, such as interacting with a foot pedal or button, speaking a voice command, or another similar input, to cause the registration touch to be recorded. In some versions, calibration instrument (134) includes a contact sensor (not shown) that senses when the distal tip (135) contacts the face of the patient. In some such versions, the operator must press distal tip (135) against the face of the patient with enough force to overcome a threshold for the contact sensor to register the contact between distal tip (135) and the face of the patient.

It should also be understood that while distal tip (135) will be contacting registration points on the patient's head or face instead of the positionally tracked tip of the guidewire (140) contacting those registration points, the system may readily make the necessary adjustments in the registration and calibration algorithms in view of the fact that the width of the wall of the rigid elongate body (138) is fixed and known.

The calibration instrument (134) or probe of FIG. 2 may provide rigidity to the flexible guidewire (140) during the registration process, which can address one source of inaccuracy (e.g., flexing of the positionally tracked guidewire during the touch). However, it does not address other sources of inaccuracy, for example, that introduced due to the flexibility or pliability of flesh on a patient's head or face as the distal tip (135) is pressed against it during the registration process. Various points on a patient's face may depress several millimeters under the force of the calibration instrument (134), which can provide a significant inaccuracy in the context of a ENT or other surgical procedure.

Figure 3:
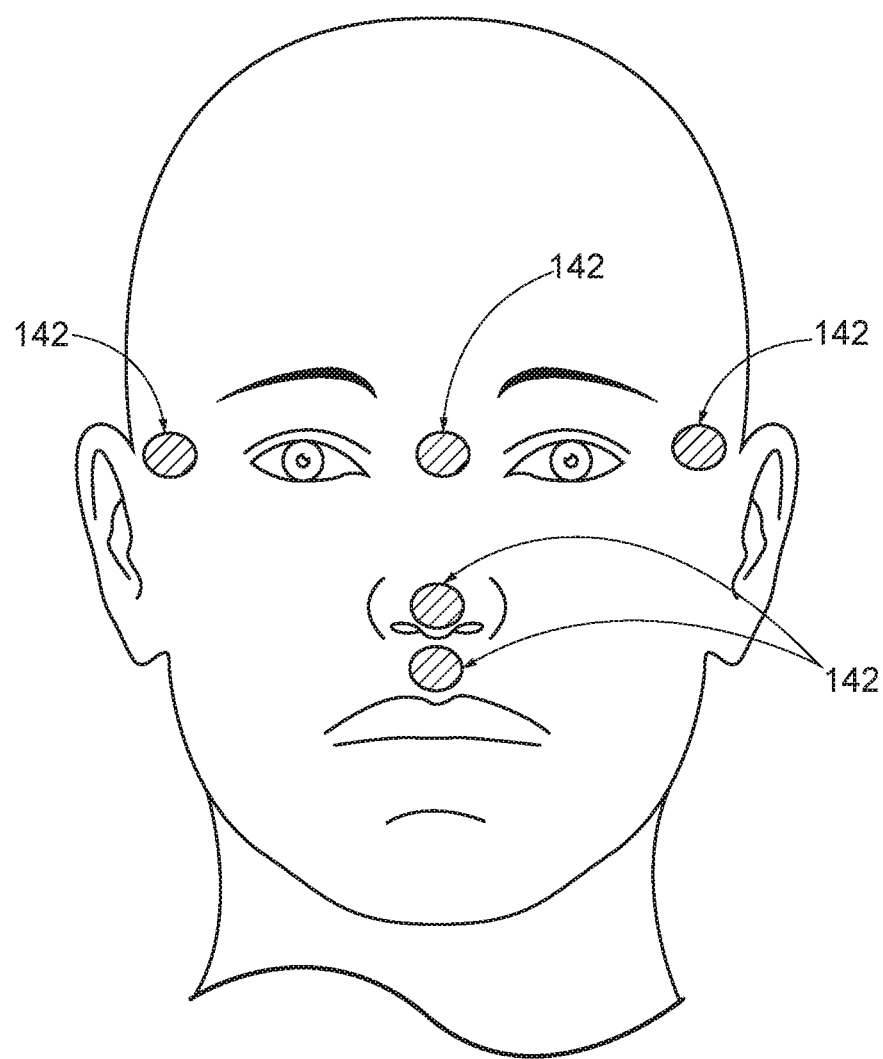
FIG. 3 is a front elevation view of a patient during a registration procedure using the registration probe of FIG. 2.

FIG. 3 shows a front elevation view of a patient showing a patient registration procedure using the calibration instrument (134). The view of FIG. 3 might be rendered on a display of the IGS system (100) during a procedure, and may show one or more registration points (142) that must be calibrated or registered using the calibration instrument (134). The registration points may, for example, be shown in one color before they are registered with a touch of the calibration instrument (134), and may change to a different color or otherwise indicate calibration after a touch of the calibration instrument (134). In some versions, one or more lasers are used to project the registration points (142) on the face of the patient, such that the operator must engage the face of the patient with distal tip (135) at each point illuminated by the laser(s).

In addition to the foregoing, calibration instrument (134) may be configured and operable in accordance with at least some of the teachings of U.S. Pub. No. 2017/0119473, entitled "System and Method for Navigation of Surgical Instruments," published May 4, 2017, the disclosure of which is incorporated by reference herein.

As can be seen from the example of FIG. 3, this registration may require five touches of the calibration instrument (134) at different points of the patient's face to be completed. In real world use, the number of registration points can be in the tens or even hundreds. In this context, it becomes apparent that it can be a very time-consuming process to identify, locate, and touch each required point.

III. EXEMPLARY SENSOR ARRAY FOR REGISTERING AND CALIBRATING AN IMAGE GUIDED SURGICAL SYSTEM

Figure 4:
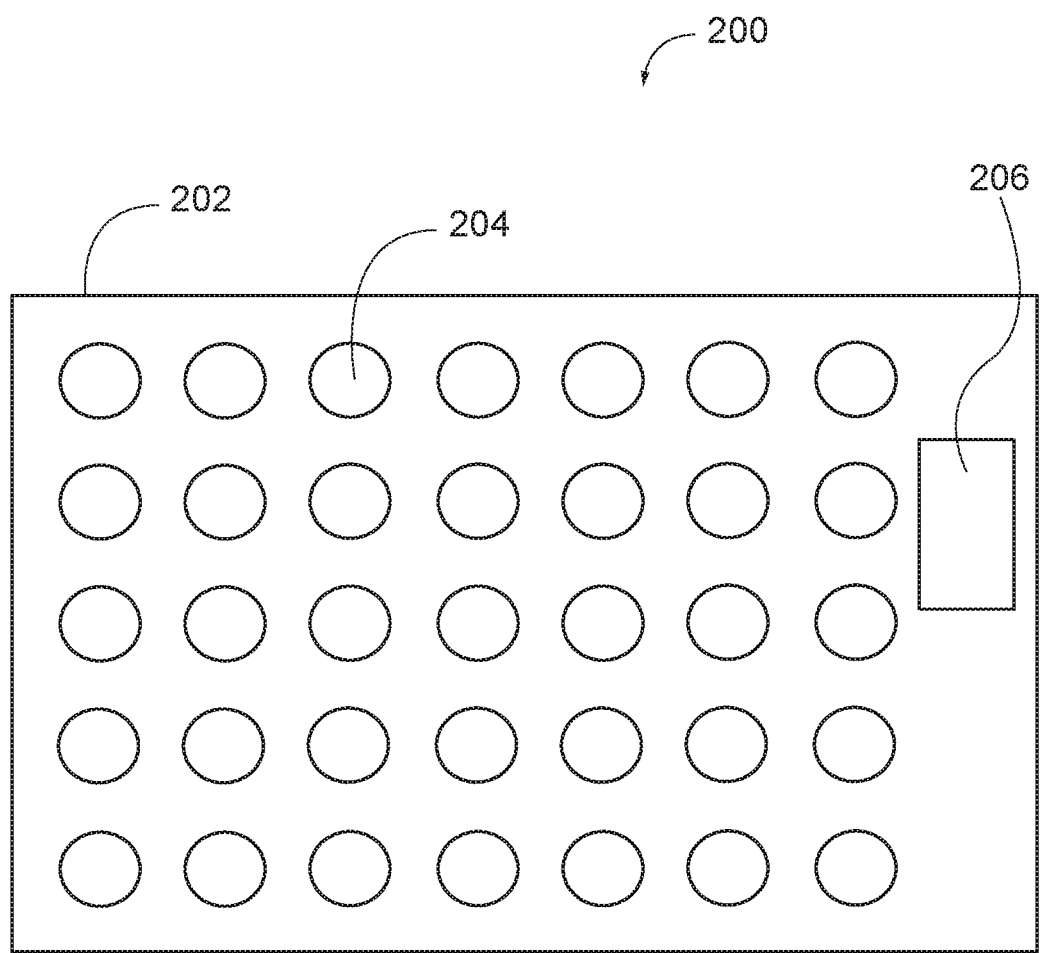
FIG. 4 is a front elevation view of an exemplary sensor array.
Figure 5:
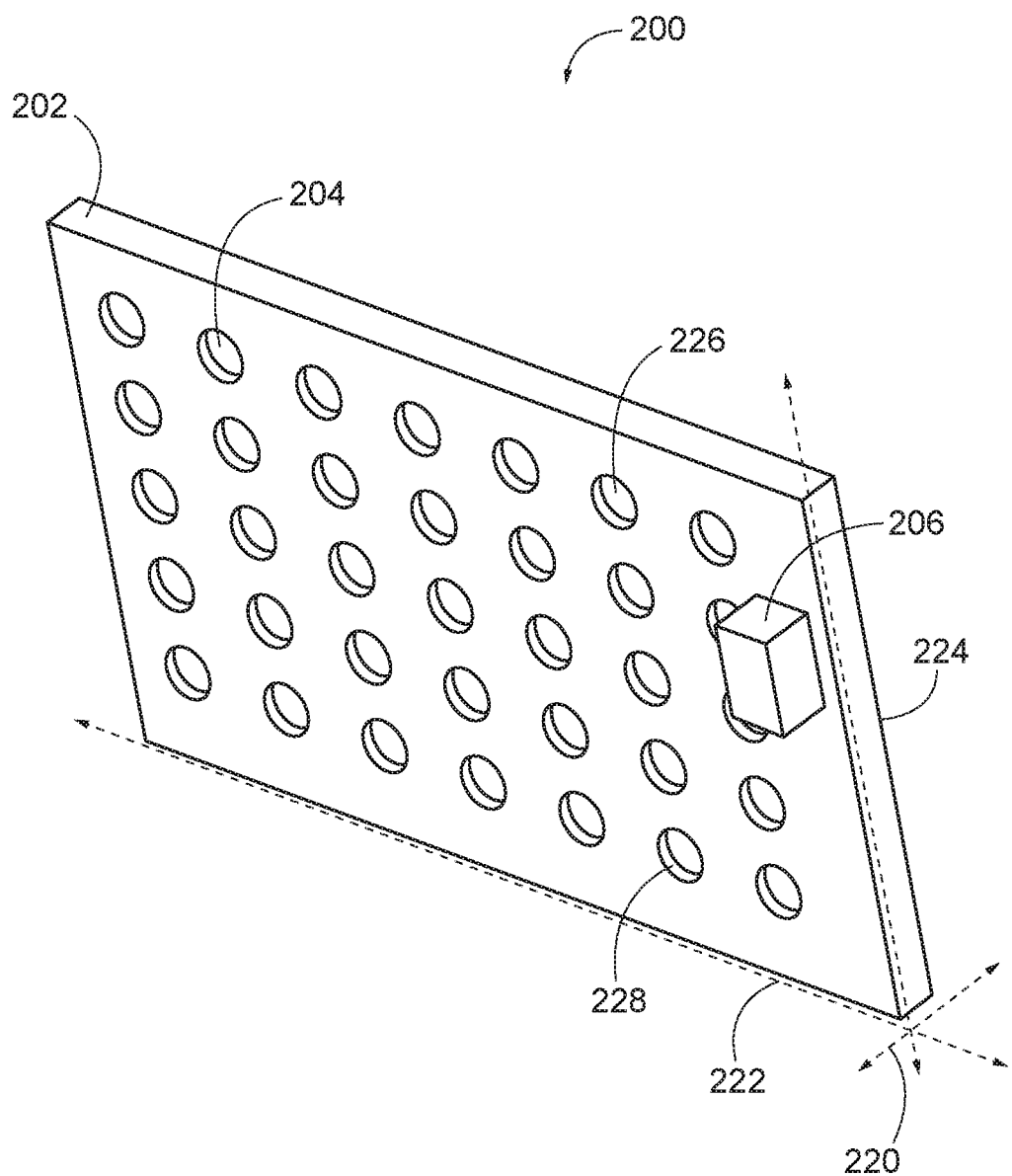
FIG. 5 is a front perspective view of the sensor array of FIG. 4.
Figure 6:
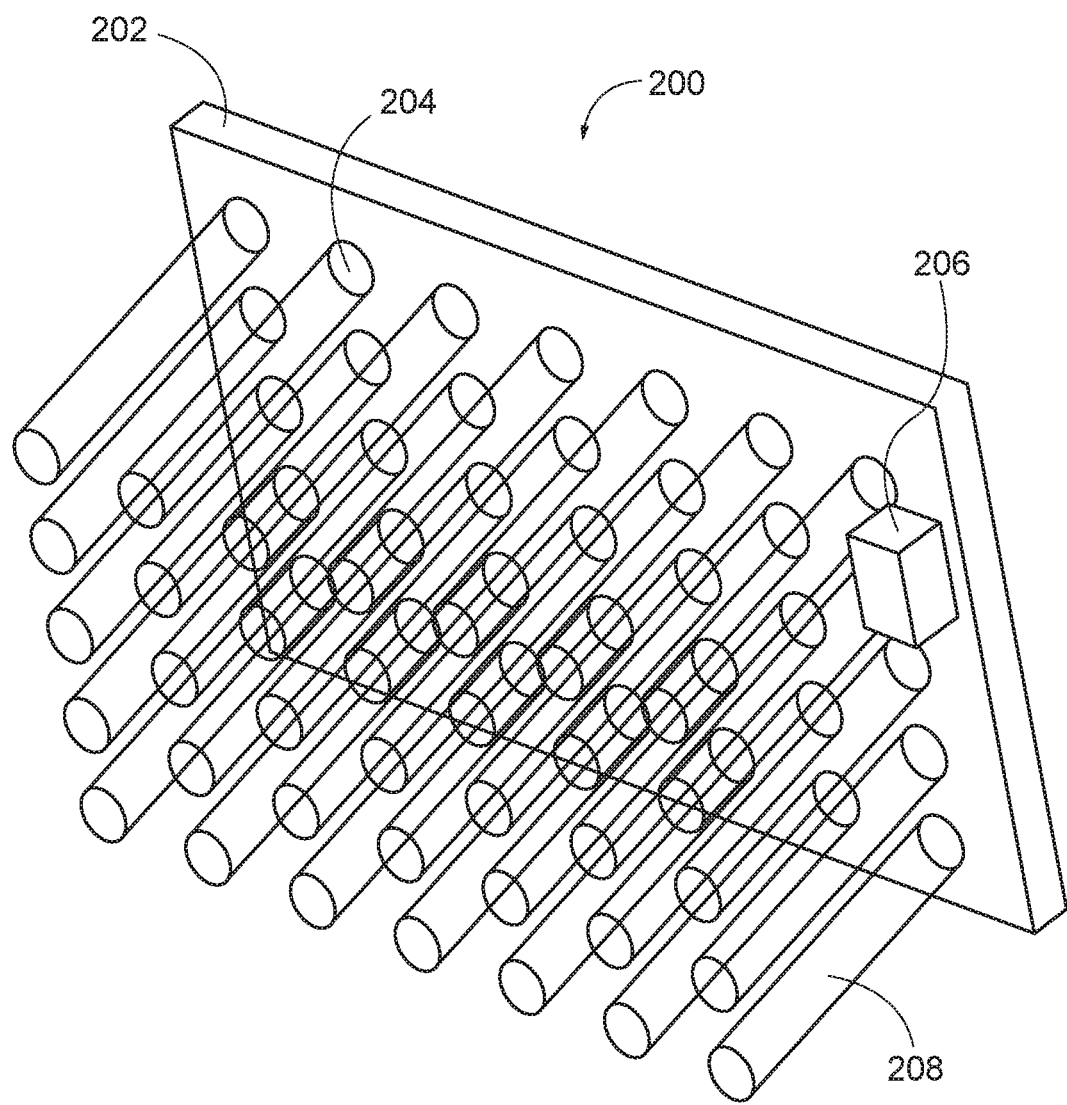
FIG. 6 is a front perspective view of the sensor array of FIG. 4 during activation and a visualization of the sensor array's zone of detection.

FIGS. 4-6 show an exemplary sensor array (200) that may be used to perform patient registration instead of or in addition to a touch-based calibration instrument (134). The exemplary sensor array (200) comprises a case (202), a plurality of sensors (204), and a position sensor (206). The plurality of sensors (204) may comprise, for example, a set of optical sensors, ultrasonic sensors, or other proximity sensors that transmit a probe signal (e.g., a projected light, ultrasonic sound waves, electromagnetic waves, etc.) and then receive a corresponding response signal (e.g., a reflected light, reflected sound, reflected electromagnetic waves, etc.). The period of time between probe signal transmission and receipt of the response, or the strength or other characteristics of the response signal, may then be used to determine the distance between the sensor's signal transmitter and the target that the probe signal strikes. Other suitable forms that sensors (204) may take will be apparent to those of ordinary skill in the art in view of the teachings herein.

Position sensor (206) may comprise one or more of an accelerometer, magnetic, or wireless beacon sensor that may be used to determine the location and orientation of sensor array (200) within three-dimensional space. An accelerometer based sensor may be able to determine movements and rotations of the sensor array (200) from a neutral point, which may be used to determine its real-time location at any time. Magnetic or other wireless sensors may operate in a manner similar to that described in relation to navigation guidewires, and may require a tracking element or receiving element located in the sensor array (200), and a tracking device or transmitting device located elsewhere in the procedure area and configured to identify the position of the tracking element at any time. Other suitable components that may be used to form position sensor (206) will be apparent to those of ordinary skill in the art in view of the teachings herein.

As noted above, patient registration may be used to identify the location of landmarks of a patient's face or other surgical site within three-dimensional space so that a set of preoperatively obtained images can be calibrated or otherwise synchronized with the real-world procedure setting. In order to accomplish this, the location of sensor array (200) within three-dimensional space must be known, and the distance between sensor array (200) and the patient's face or other surgical site must be known. These variables can then be used to determine the location of landmarks or other positions on a patient's face or other surgical site within three-dimensional space. For example, in the case of a laser sensor, a laser beam may be produced by the source sensor (204), and the laser beam may strike a target across a distance of x-millimeters. A portion of the laser beam will be reflected off the target, with such reflected or scattered light being detected by source sensor (204). The period of time between laser projection and reflection detection may then be used to determine the x-millimeter distance that separates source sensor (204) and the target. If the position of source sensor (204) along the z-axis is "Z," as determined by the position sensor (206), then the position of the target along the z-axis can be determined as (Z+/−x-millimeters).

As can be seen in FIG. 5, the plurality of sensors (204) are positioned at the same point along the z-axis (220) of the case (202). While this configuration may be adequate, it should also be understood that sensors (204) may be placed at different points along the z-axis (220) (e.g., to allow for differently shaped cases (202)), as the sensor's (204) initial position may be compensated for as long as it remains substantially static relative to the position sensor (206). To assist in this, the case (202) may be made of any substantially rigid material, such as plastics or metals, so that the front face of the case (202) on which the plurality of sensors (204) are placed will not flex under its own weight or during use. Such flex would result in a change of the sensors' (204) initial position along the z-axis (220) as reported by the position sensor (206), which may skew determination of the target's position within three dimensional.

In addition to being able to provide the position of the sensor array (200) within three-dimensional space, the position sensor (206) may also determine its orientation within three-dimensional space. This may be useful where the sensor array (200) cannot be oriented so that its front face is completely parallel to the target surface. This could occur due to space limitations within a procedure area, to allow space for clinicians to access areas around the sensor array (200), human error, or other causes. Non-parallel orientation to the target may introduce inaccuracy if not accounted for, for the same reason that flexing of the case (202) along the z-axis might. For example, referring to FIG. 5, and assuming that the target is completely parallel to the sensor array (200) as oriented in FIG. 5, if the sensor array (200) were to rotate around the x-axis (222) even slightly, an upper sensor (226) of the sensor array (200) could shift to be several millimeters closer to the target as compared to a lower sensor (228) in the same column. If this orientation is not known or accounted for, the position of a point of the surgical site detected by the uppers sensor (226) could be inaccurately registered and calibrated within the three-dimensional space.

The position sensor's (206) orientation determining capability may detect that the sensor array (200) is not completely parallel to the target, and either warn an operator that sensor array (200) needs to be re-oriented. Alternatively, sensor array (200) (and/or some other system component) can adjust the data provided by each individual sensor (204) of the plurality of sensors (204) to account for the non-parallel orientation. This could include, for example, determining that, due to its orientation, the upper sensor (226) is x-millimeters closer to the target as compared to the lower sensor (228), and adjusting the calculations accordingly during calibration and registration.

Figure 8:
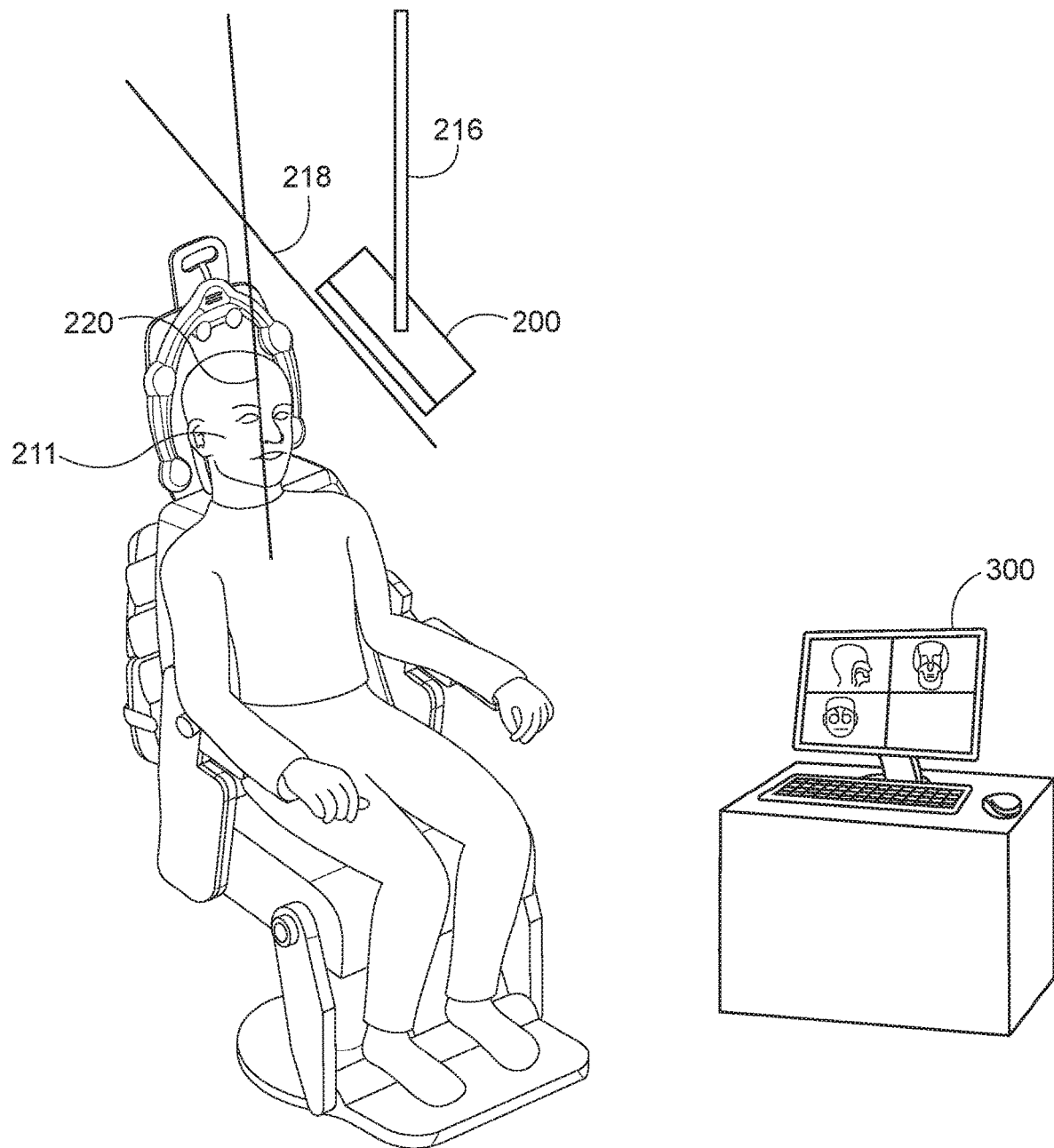
FIG. 8 shows a front perspective view of a surgical procedure area using the sensor array of FIG. 4.

FIG. 8 shows an exemplary scenario where a sensor array (200) is not positioned and oriented so that it is substantially parallel to the target. As can be seen, the sensor array (200) is suspended from an arm (216) and is located above the target area (211), but is not oriented on the arm (216) so that it is substantially parallel to the target area (211), as can be seen by the intersecting lines (218, 220) drawn parallel to the sensor array (200) and the target area (211). In some implementations, the arm (216) may provide a wide range of manual or automatic motions to support a wide range of positions and orientations for an attached sensor array (200) relative to the target area (211). Some implementation may also include an orientation indicator that may comprise, for example, a lighted indicator, an audible indicator, or a haptic indicator configured to notify a user when the sensor array is substantially parallel to the target area (211) which may aid in manual positioning and orientation of the sensor array (200). In implementations including an arm (216) with automated features, the arm (216) may automatically adjust the position and orientation of the sensor array (200) relative to the target area (211) as it is activated or manually moved by a user, in order to maintain a substantially parallel orientation.

Figure 7:
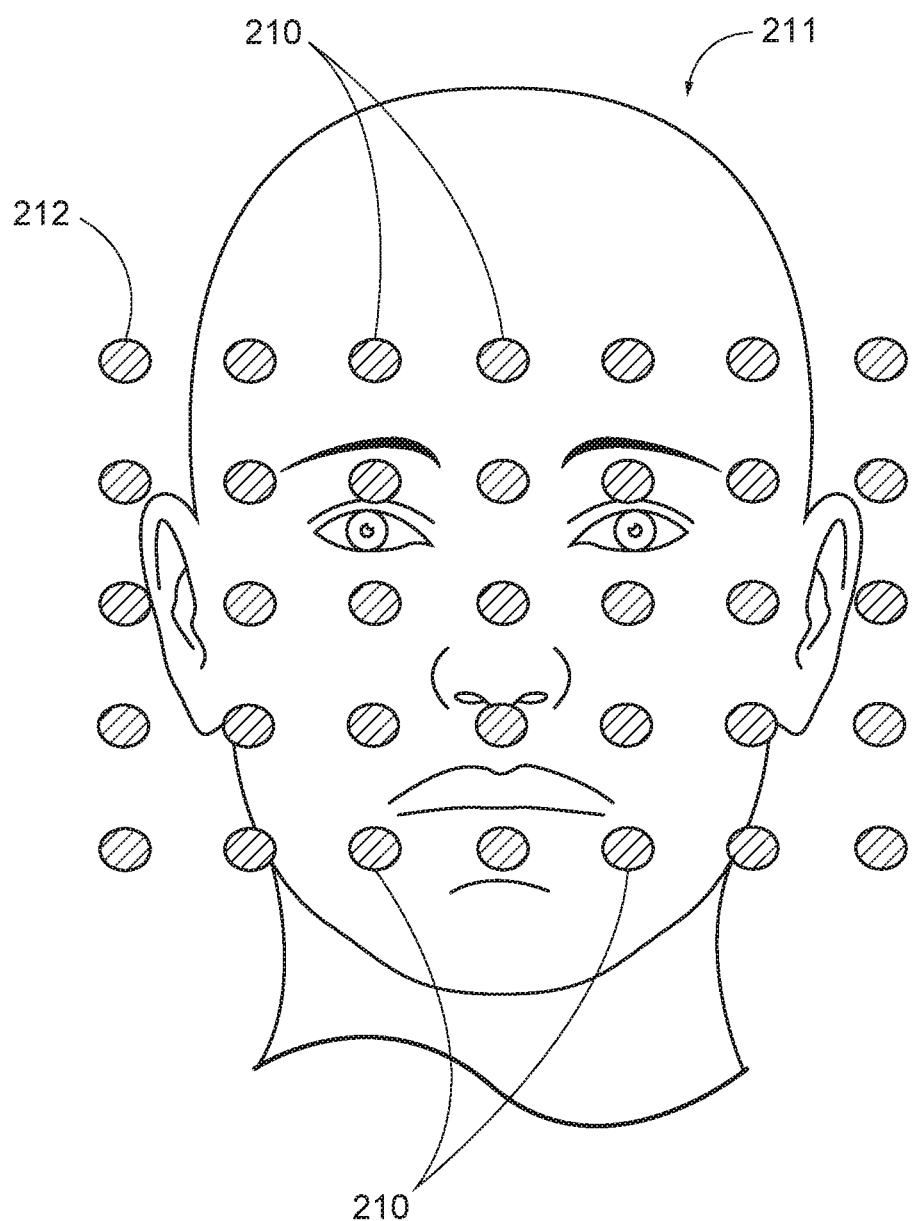
FIG. 7 is a front elevation view of a patient during a registration procedure using the sensor array of FIG. 4.

FIG. 6 shows the sensor array (200) during activation with a simulated visualization of the area (208) that is within the sensing or detection range of the plurality of sensors (204). FIG. 7 shows a simulated visualization of a number of registration points on a patient's face that may be simultaneously detected and registered by the exemplary sensor array (200). As can be seen, a plurality of registration points (210) can be simultaneously registered by the large detection area (208) of the sensor array (200). Due to variations between the size of a patient's head and the sensor array (200), the probe signal transmitted by some of the sensors may miss the patient's head entirely (212). In such cases, the response signal may not be received by the source sensor (e.g., where the distance to an incidental target is too great, or where the patient's head is laid against a surface that does not result in a response signal), or the response signal may be received and the calculated distance to the target determines that a point beyond the patient's face has been measured. In such cases, data generated by the sensor that is not striking the patient's face may be filtered or otherwise disregarded for registration purposes, while valid registration points (210) may be registered in order to locate the patient's facial landmarks in three-dimensional space.

Use of the exemplary sensor array (200) may provide several advantages as compared to a touch calibration instrument (134). As can be seen in FIGS. 6-7, the sensor array (200) can register a plurality of points (210) simultaneously, and can be scaled to any desired number or affected area by varying the size of the sensor array (200) and/or the number and arrangement of the plurality of sensors (204). In comparison to the potentially time consuming point-by-point registration offered by a touch calibration instrument (134), a sensor array (200) may complete registration by simply positioning and orienting it be substantially parallel to the target (e.g., by moving an arm, gimble, or other apparatus such as the arm (216) shown in FIG. 8 for suspending the sensor array (200) above a patient), and activating the sensor array (200) to capture the distance between the sensors and the target, which can then be used to calculate the target's position in three-dimensional space. Reducing the time required for registration can improve the patient's experience during a procedure, and make more efficient use of procedure rooms, equipment and staff. Additionally, as has been discussed, using a touchless registration system such as the exemplary sensor array (200) can result in more accurate positioning of the target within three-dimensional space because it reduces or eliminates the potential for flexibility of a touch calibration instrument (134) or deformation of the patient's skin to introduce inaccurate registration data into the process.

IV. EXEMPLARY METHODS FOR USING A SENSOR ARRAY FOR REGISTERING AND CALIBRATING AN IMAGE GUIDED SURGICAL SYSTEM

Figure 9:
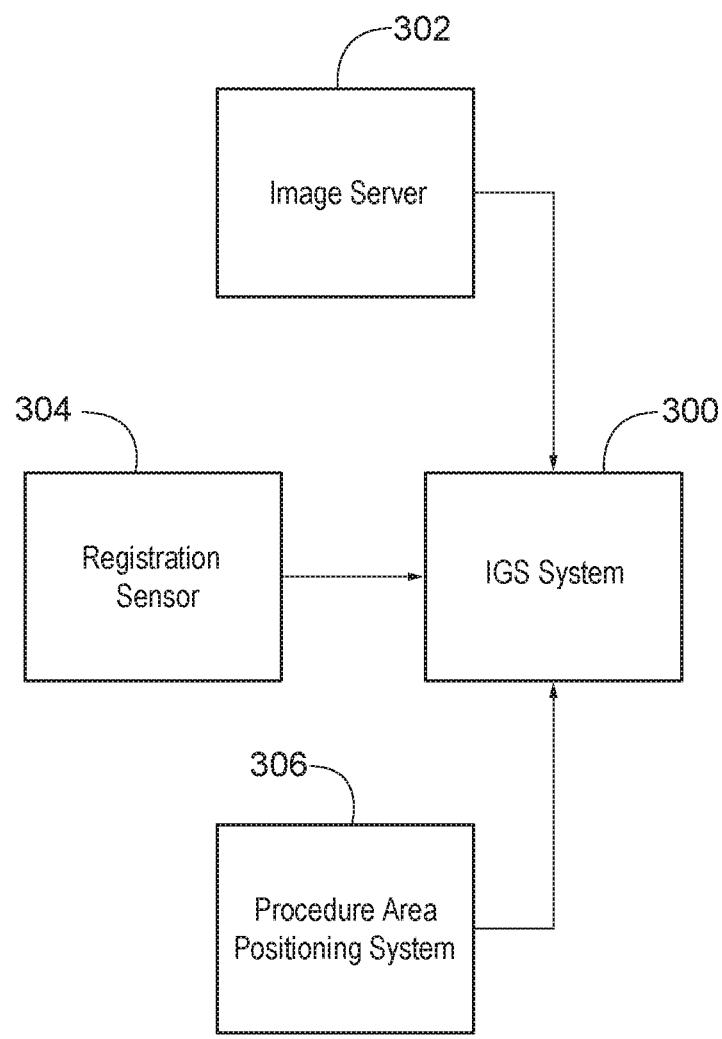
FIG. 9 shows a system diagram of an exemplary image guided surgery system.
Figure 10:
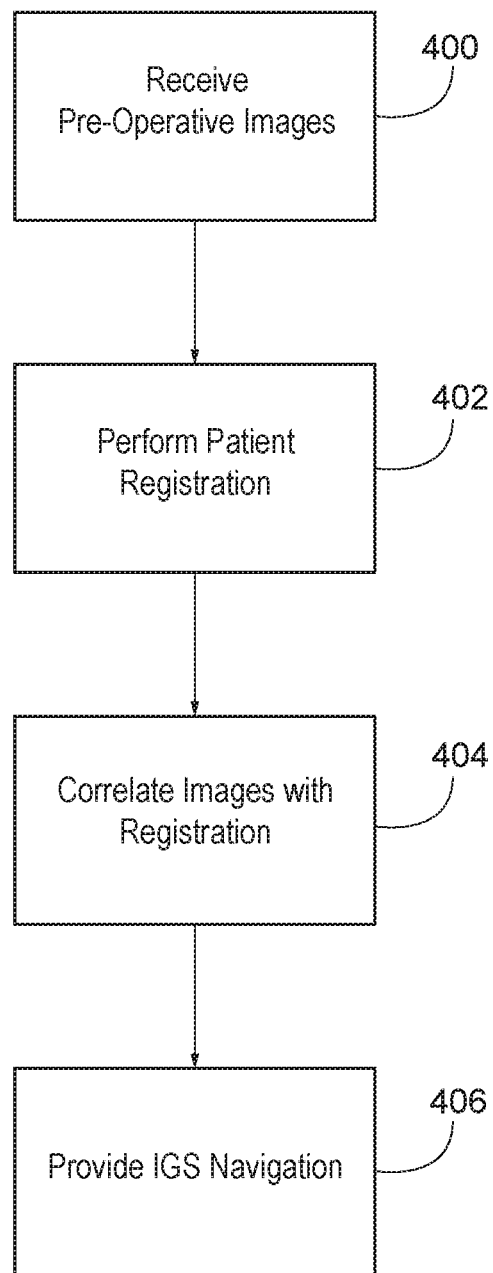
FIG. 10 shows an exemplary set of high level steps that may be performed with an image guided surgical system to register a patient.
Figure 11:
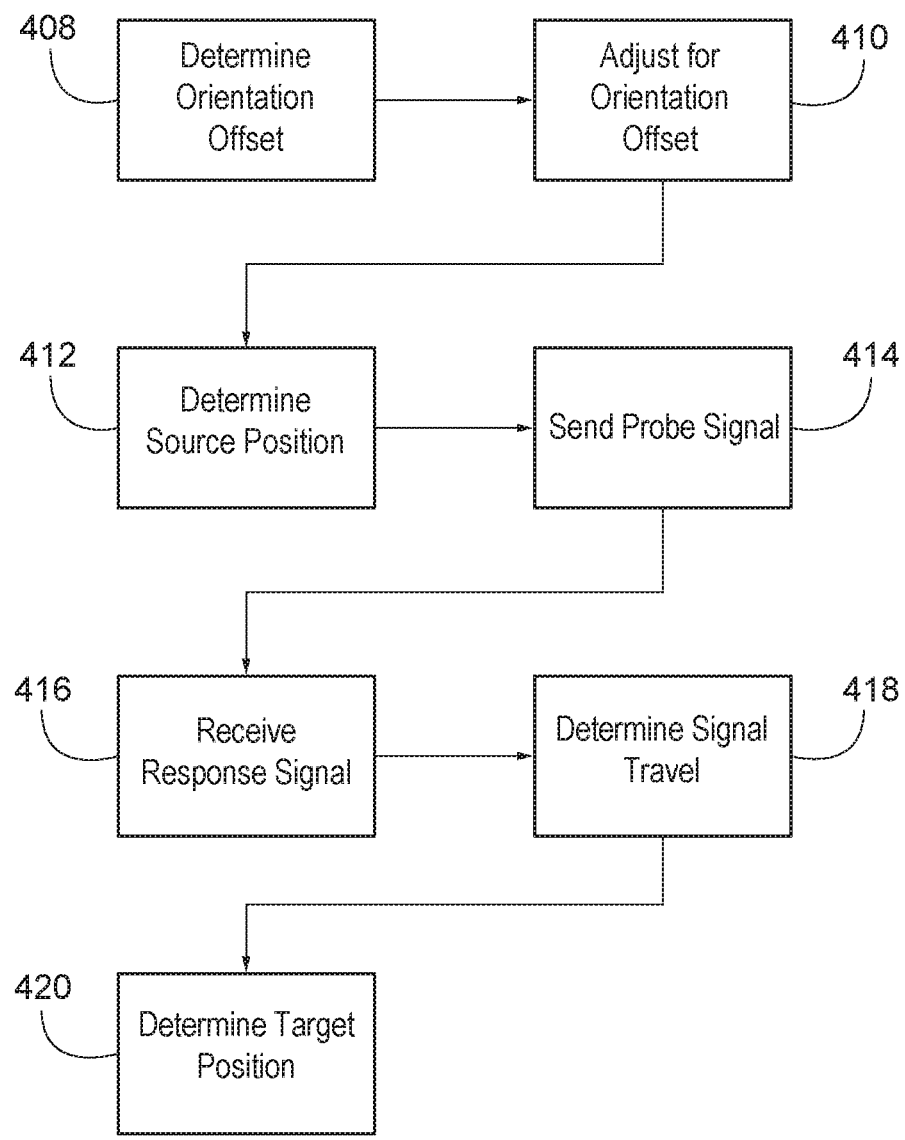
FIG. 11 shows an exemplary set of steps that may be performed with an image guided surgical system to generate and process data from the sensor array of FIG. 4.

FIGS. 10-11 show methods for touchless facial registration of an image guided surgical system that may be performed by a system such as that shown in FIG. 9. The exemplary system of FIG. 9 comprises an image guided surgery or IGS system (300), an image server (302), a procedure area positioning system (306), and a registration sensor (304). It should be understood that the components of the exemplary system, and their function as described are example only and could be implemented in a variety of ways. For example, some features could be performed by either the IGS system (300), the registration sensor (304), or both, in some implementations. Similarly, some components may be combined or divided into further components. For example, functions performed by the IGS system (300) may be performed across several components (e.g., an IGS system (300), a cloud computing system, a handheld IGS device, or others), or the functions of the IGS system (300) and image server (302) could be combined and performed by a single component or device. Such variations will be apparent to one of ordinary skill in the art in light of this disclosure.

The IGS system (300) may comprise a computer having components such as a processor and memory, storage, display, and various user and communication interfaces. The IGS system (300) may be configured to receive information from one or more of the area positioning system (306), the registration sensor (304), the image server (302), and/or other data sources. Information received by the IGS system may be used to prepare and display or otherwise provide information such as images, sounds, video, and software tools to assist in the performance of a surgical procedure. Received information may comprise, for example, pre-operational images, video, and data from the image server (302) or another system, facial landmark registration from a registration sensor (304), procedure area positioning and orientation data for tools and other objects within the procedure area from the area positioning system (306), and other similar data. Using this data, the IGS system (300) may, for example, track a number of positionally tracked devices within three-dimensional space, and map a registered patient within that three-dimensional space so that pre-operative images may be accurately associated with images generated during a procedure.

The image server (302) may be one or more remotely or locally located servers that may store pre-procedure information, procedure information, and post procedure information, which may include pre-operative images, locations and orientations of instruments, devices, and other tracked objects during a procedure, and post-procedure analysis or other metrics that may aid in the assessment of the performance of a procedure.

Figure 12:
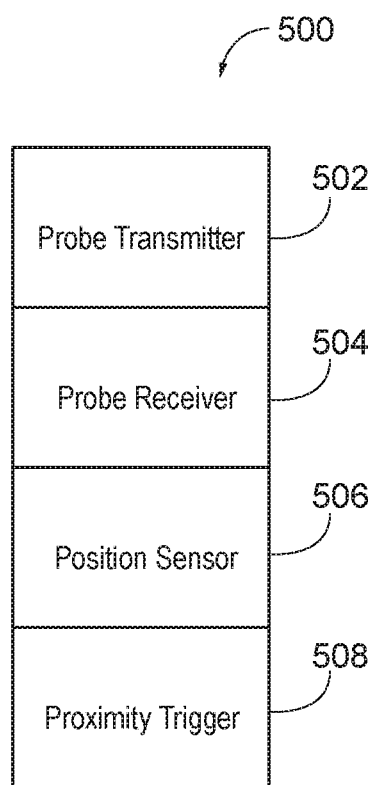
FIG. 12 is a schematic diagram of an exemplary touchless sensor probe that may be used to register a patient.

The registration sensor (304) may comprise, for example, a sensor array (200), or another registration instrument such as the exemplary sensor probe (500) of FIG. 12. The registration sensor (304) is configured to provide some or all of the information required to locate the target area (211) (e.g., a patient's facial landmarks) within three-dimensional space, as has been described in relation to the sensor array (200). This could include, for example, determining the distance between a source sensor (204) and a target. The area positioning system (306), which may be, for example, a tri-axis sensor as described in relation the position sensor (206), may provide any additional information that is needed to locate the target area (211) within three-dimensional space, which could include, for example, determining the position of the source sensor (204). The components of the system of FIG. 9 may be in communication with the IGS system (300) and, in some implementations, with each other, via various forms of wired and wireless communication.

FIG. 10 shows a set of high level steps that may be performed using the system of FIG. 9 in order to register a patient in three-dimensional space using a registration sensor (304), which will allow for IGS navigation features to be provided at the IGS system (300). The exemplary steps comprise receiving pre-operative images (block 400), receiving patient registration (block 402), correlating the pre-operative images with the patient registration (block 404), and providing IGS navigation (block 406). Receiving pre-operative images may comprise, for example, requesting and/or receiving one or more data sets from an image server (302), local storage, or another similar device. Received information may then be stored locally to the IGS system (300) and kept readily available so that it may be quickly accessed during IGS navigation.

Performing the patient registration (block 402) may comprise activating a registration sensor (304) in order to produce a set of data indicating the distance between the registration sensor (304) and the target area (211), in the form of one or more registration points that can be used to locate landmarks or other physical features of a patient's face or other target area (211) features, and may also include using an area positioning system (306) to determine the location of the registration sensor (304), so that the patient's face can be located within three dimensional space relative to the area positioning system (306). Correlating pre-operative images with the registration data may comprise selecting one or more of the pre-operative images and mapping them within three-dimensional space relative to the target area (211). Providing IGS navigation (block 406) may then be performed by using an accurate three-dimensional mapping of the pre-operative images relative to the target area (211). This allows for the IGS system (300) to accurately display the positions of presently tracked objects (e.g., guidewires or other positionally tracked instruments) in the context of the pre-operative images during a procedure where IGS navigation is used.

FIG. 11 shows an exemplary set of steps that may be performed when performing a patient registration (block 402) with a registration sensor (304). These steps may be performed by the IGS system (300), the registration sensor (304), and/or another device having appropriate processing, memory, and storage capabilities, and may be performed in varying orders or in parallel in some implementations, unless the nature of a particular step which requires, as input, data that becomes available only upon completion of a prior step. The IGS system (300) may determine an orientation offset (block 408) based upon orientation data associated with the registration sensor (304) and the target area (211) in order to determine whether they are substantially parallel. This could include using data provided by the positioning sensor (306) to determine the current orientation of the registration sensor (304), using a positioning sensor in a piece of equipment worn by or attached to a patient, or a patient table or chair to determine the current orientation of the target area (211), or by using configured static orientation values for the registration sensor (304) and/or target area (211) that may have been determined automatically or manually at a prior time (e.g., by statically positioning a patient chair in a known orientation) and configured within the IGS system (300).

Once an orientation offset has been determined (block 408), if the registration sensor (304) and target area (211) are not substantially parallel, the IGS system (300) may adjust one or more variables to account for this offset (block 410). This could include, for example, increasing or reducing the measured distance between a source sensor and a target to account for a non-parallel orientation, as has been previously described. The IGS system (300) may also determine a source position (block 412) for the registration sensor (304). As with determining orientation, this may include determining a current position using information from a position sensor (206, 506) or other area positioning system (306), or using a pre-determined static value where it is possible for a registration sensor (304) to be statically fixed in position.

The IGS system (300) may also send a probe signal (block 414) by activating one or more sensors of a registration sensor (304), and receive a response signal (block 416) that is reflected, echoed, or otherwise returned from the target area (211) and captured by a photo eye, microphone, or other receiver. After receiving the response signal (block 416), the IGS system (300) may determine the signal travel time and distance (block 418). When determining signal travel distance (block 418), the IGS system may account for any orientation offset for particular sensors that may have been earlier determined (block 410). After signal travel distance (block 418) and signal source position (block 412) have been determined and are available to IGS system (300), the system may determine (block 420) and store the target area (211) position. Once the target position is known (block 420), the IGS system may use that position to correlate pre-operative images (block 404) with the target area (211) and provide IGS navigation (block 406).

V. EXEMPLARY ALTERNATIVE SENSOR PROBE FOR REGISTERING AND CALIBRATING AN IMAGE GUIDED SURGICAL SYSTEM

Figure 13:
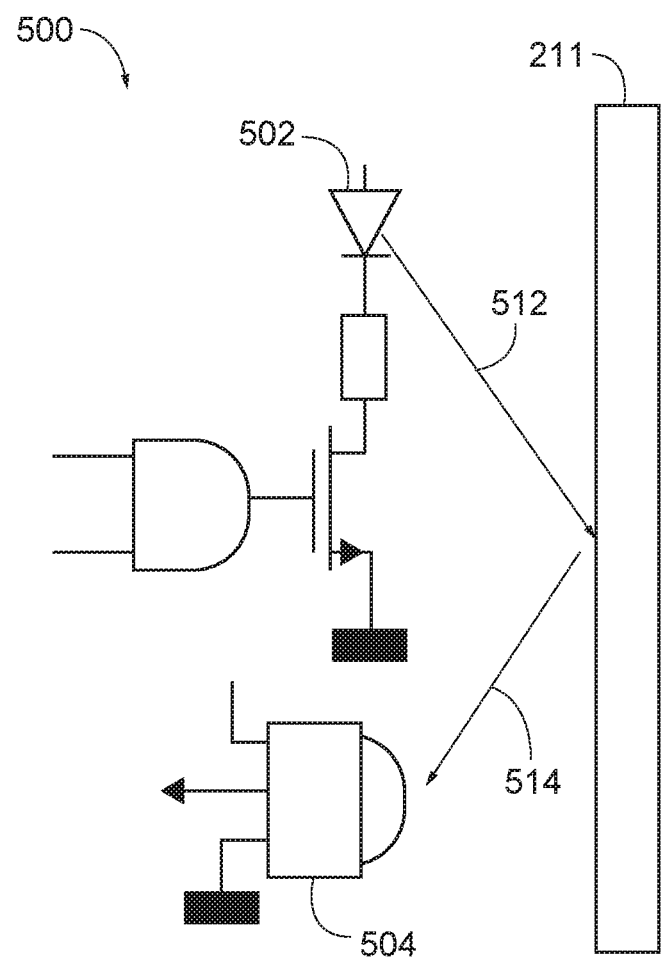
FIG. 13 is a schematic diagram of a tip of the exemplary touchless sensor probe.

FIGS. 12-13 show an exemplary alternative sensor probe that may be used to, in a manner similar to previously discussed touch probes such as the calibration instrument (134), register a patient one point at a time. The probe (500) shown in FIG. 12 comprises a probe transmitter (502), a probe receiver (504), a position sensor (506), and a proximity trigger (508). While probe transmitter (502) and probe receiver (504) are shown as separate components, probe transmitter (502) and probe receiver (504) may in fact be integrated into a single component in some variations. The probe (500) could be implemented in a variety of forms, for example, a housing similar to the elongate body (138) of the calibration instrument (134) could contain or be attached to one or more of the components of FIG. 12. A housing or body such as that of the calibration instrument (134) may be a desirable form for the probe (500) because the stylus-like shape may be comfortable and familiar to users (e.g., grasping probe (500) with a pencil grip).

When registering a point on a target area (211), the probe (500) operates in a manner similar to the sensor array (200). The probe transmitter (502) and probe receiver (504) may be positioned towards the tip end of the probe (e.g., at the rounded distal tip if the probe (500) were implemented in a form similar to that of FIG. 2), and, when activated, function similarly to a sensor (204) of the sensor array (200) as described above. In particular, the probe transmitter (502), which could comprise an optical transmitter, ultrasound transmitter, or other wireless transmitter, will transmit a probe signal (512) towards the target area (211), as shown in FIG. 13. The probe signal will reflect, echo, or otherwise return from the target area (211) and be received by the probe receiver (504) as a response signal (514). The time of travel between the probe signal transmission and receipt of the response signal can be used by an IGS system (300) or another processing device to determine the distance between the probe (500) and the target area (211). This distance, combined with a position and orientation of the probe (500) as supplied by a position sensor (506) may then be used to determine the registered point of the target area (211) in three-dimensional space. The position sensor (506) may comprise a tri-axis sensor, accelerometer based positioning sensor, magnetic positioning sensor, or other positioning sensor that may function as or function with the area positioning system (306) in order to provide a position and orientation of the probe (500).

The proximity trigger (508) of the probe (500) may itself comprise a sensor, or may be a feature or configuration of the probe transmitter (502) and probe receiver (504) that is configured to determine real-time proximity relative to the target area (211) and, when it is within a certain proximity of a target, capture and register a point of the target area (211). This allows for the probe (500) to automatically activate and register points when positioned proximately to the target area (211), so as to avoid the need for a user clicking a button, foot pedal, or making contact with the target area (211) with force above a certain threshold in order to capture the registration point data. In this manner, the user may move probe (500) about the target area (211) within a proximity that causes the proximity trigger (508) to register points of the target area (211) in order to complete the registration process. In effect, this would allow the probe (500) to rapidly register a number of points across the target area (211) without substantially pressing against any point of the target area (211) or taking other actions to trigger the registration that may reduce the accuracy of the registration.

In some variations, probe (500) comprises a capacitive sensor or a resistive sensor, either of which may be used to effectively form (or serve as a substitute for) the combination of probe transmitter (502) and probe receiver (504). In such variations, the capacitive sensor or resistive sensor may be able to detect contact with a patient's face and thereby register the position, with a relatively light touch on the patient's face. In other words, an operator need not press probe (500) against the patient's face with substantial force in order to activate a capacitive sensor or a resistive sensor through contact with the patient's face. Thus, during normal use of probe (500), there is little to no risk of deforming the patient's face to the point where position data will be inaccurate.

As noted above in the context of calibration instrument (134), probe (500) may be used in conjunction with one or more lasers that are used to project the registration points (142) on the face of the patient, such that the operator must use probe (500) to register the locations of each point illuminated by the laser(s) on the patient's face. While use of the probe (500) may be slower than the sensor array (200), it may also be much faster than the use of a probe such as the calibration instrument (134). The probe (500) may provide additional beneficial features, such as ease of use, reduced complexity (e.g., one sensor rather than an array of sensors), reduced power consumption, increased mobility (e.g., handheld rather than arm or ceiling mounted), reduced cost, and other similar benefits that will be apparent to one of ordinary skill in light of this disclosure.

As can be seen, registration sensors may be implemented in a variety of forms beyond those of a sensor array (200) or a probe (500). This could include, for example, a single row of sensors disposed along a longitudinal member that can be passed across a target area, one or more rows of sensors disposed along a curved member that can be rotated around a target area, or other similar configurations.

To the extent that the various kinds of sensors that are described herein (e.g., optical sensors, ultrasonic sensors, proximity sensors, capacitive sensors, resistive sensors, etc.) as being usable in sensor array (200) and probe (500) are known in industrial/manufacturing settings (e.g., tracking objects in an assembly line, etc.), it will be understood that the present context is substantially different. In industrial/manufacturing settings, tracked objects may be more likely to have consistent surface geometry (e.g., the sensed surface is flat), consistent surface coloring, and/or other consistent properties. However, in the present context of medical procedures involving human subjects, the sensors may experience a substantially greater range in variation among the sensed surfaces. Such variations may include various surface contours, colors, lividity, and/or other variations in properties of human faces. In some instances, the sensors and/or the manner in which the sensors are operated may be modified to accommodate such variation among the sensed surfaces. For instance, optical sensors may be configured to operate on different light frequencies (e.g., sweeping through a plurality of frequencies) to more readily account for variation in skin tone among various patients. Other ways in which sensors and/or the manner in which the sensors are operated may be modified to account for variation among human face properties will be apparent to those of ordinary skill in the art in view of the teachings herein.

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system for registration of a target area, the system comprising: (a) a sensor array body; (b) a plurality of distance sensors attached to the sensor array body, wherein each of the distance sensors is positioned to be aimed towards the target area and is operable to determine a distance between a registration point of the target area and that sensor; (c) a position sensor attached to the sensor array body and operable to provide a position and an orientation of the sensor array body; and (d) at least one processor, wherein the at least one processor is configured to determine the three-dimensional location of a plurality of registered points of the target area within a procedure space based upon the distance, the orientation, and the position for each of the distance sensors.

Example 2

The system of Example 1, wherein the distance sensors are arranged in a shape selected from the group consisting of a rectangle, a square, a circle, a triangle, and an ellipse.

Example 3

The system of any one or more of Examples 1 through 2, wherein a face of the sensor array body is substantially flat, and wherein the at least one processor is contained within the sensor array body.

Example 4

The system of any one or more of Examples 1 through 3, wherein the distance sensors comprise a type selected from the group consisting of an optical sensor, an ultrasonic sensor, and a magnetic sensor.

Example 5

The system of any one or more of Examples 1 through 4, wherein the at least one processor is configured to determine the three-dimensional location of the plurality of registered points by, for each sensor of the plurality of distance sensors: (i) determining an origin position for a probe signal transmitted by that sensor, wherein the origin position indicates that sensor's position within the procedure space, based upon the position and the orientation of the sensor array body, and (ii) determining a registered point for that sensor based upon the origin position and a distance traveled by the probe signal before striking the registration point of the target area.

Example 6

The system of Example 5, wherein the at least one processor is further configured to: determine an orientation of the target area relative to the sensor array body, where the target area and the sensor array body are not substantially parallel, determine, for each sensor of the plurality of distance sensors, an offset value, and determining the registered point for that sensor based upon the origin position, the distance traveled by the probe signal, and the offset value.

Example 7

The system of Example 6, further comprising a target area orientation sensor configured to provide an orientation of the target area to the at least one processor.

Example 8

The system of any one or more of Examples 1 through 7, wherein a navigation processor of the at least one processors is configured to: associate the plurality of registered points with a set of pre-operative images of the target area, and provide an image guided surgery navigation interface during a procedure based upon the association of the plurality of registered points, the set of pre-operative images, and a set of instrument data provided by a position sensor of a surgical instrument used during the procedure.

Example 9

The system of any one or more of Examples 1 through 8, wherein the distance sensors are configured to be positioned and operable at a distance of between about 4 inches and 20 inches from the target location when the location of the plurality of registered points is determined.

Example 10

The system of any one or more of Examples 1 through 9, further comprising an orientation indicator, wherein the orientation indicator is configured to provide an indication to a user when the sensor array body is not substantially parallel to the target area.

Example 11

The system of any one or more of Examples 1 through 10, further comprising an automated arm, wherein the automated arm is operable to orient the sensor array body so that it is substantially parallel to the target area.

Example 12

The system of any one or more of Examples 1 through 11, wherein the plurality of distance sensors comprises at least 30 individual sensors, and wherein the plurality of distance sensors are positioned on the sensor array body such that the transmitted probe signals strike substantially all of the target area.

Example 13

The system of any one or more of Examples 1 through 12, wherein the at least one processor is further configured to, for any sensor of the plurality of distance sensors whose probe signal falls outside of the target area during use, disregard proximity data from that sensor.

Example 14

The system of any one or more of Examples 1 through 13, wherein the plurality of distance sensors are configured to be activated once in order to gather the data used to determine the three-dimensional location of the plurality of registered points.

Example 15

A registration probe comprising: (a) an elongate body adapted to be held by a user, the elongate body comprising a distal tip; (b) a target sensor located at the distal tip, wherein the target sensor is operable to detect the presence of a patient's face in front of the distal tip, without requiring the distal tip to be pressed into the patient's face; (c) a position sensor operable to provide a position and an orientation for the touchless registration probe; and (d) at least one processor configured to: (i) activate the target sensor, (ii) determine the three-dimensional location of the target within a procedure space as a registered point based upon a signal from the target sensor, and (iii) determine the position and orientation of the registration probe at the time the signal is received from the target sensor.

Example 16

The registration probe of Example 15, further comprising a proximity trigger configured to cause the target sensor to activate and determine the registered point when the distal tip is within a capture distance of the target.

Example 17

The registration probe of any one or more of Examples 15 through 16, wherein the target sensor comprises a capacitive sensor or a resistive sensor.

Example 18

The registration probe of any one or more of Examples 15 through 17, wherein the target sensor comprises an optical sensor.

Example 19

The registration probe of any one or more of Examples 15 through 18, wherein the position sensor comprises a type selected from the group consisting of: an accelerometer based sensor; a magnetic based sensor; a wireless beacon based sensor.

Example 20

A method for registering facial landmarks for image guided surgery navigation comprising the steps: (a) positioning a sensor array so that a plurality of distance sensors of the sensor array are directed at and substantially parallel to a target area, wherein the target area is patient's facial area; (b) activating the sensor array to capture a set of distances indicating the distance traveled by a probe signal originating from each of the plurality of distance sensors before striking a target point within the target area; (c) determining a position and an orientation of the sensor array within three-dimensional space; (d) producing a set of registered points by, for each target point within the target area, determining the three-dimensional position of that target point based upon the position and the orientation of the sensor array, and the distance traveled by the probe signal; (e) creating a navigation data set by associating the set of registered points with a set of pre-operative images; and (f) providing image guided surgery navigation based upon the navigation data set.

VII. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system for registration of a target area, the system comprising:
   (a) a sensor array body;
   (b) a plurality of distance sensors attached to the sensor array body, wherein each of the distance sensors is positioned to be aimed towards the target area and is operable to determine a distance between a registration point of the target area and that distance sensor, wherein the registration point is a point on a surface that is detected by that distance sensor;
   (c) a position sensor attached to the sensor array body and operable to provide a position and an orientation of the sensor array body; and
   (d) at least one processor, wherein the at least one processor is configured to:
      (i) determine the three-dimensional locations of a plurality of registered points within a procedure space based upon the distance, the orientation, and the position for each of the distance sensors,
      (ii) associate the plurality of registered points with a set of pre-operative images of the target area, and
      (iii) provide an image guided surgery navigation interface during a procedure based upon the association of the plurality of registered points, the set of pre-operative images, and a set of instrument data provided by a position sensor of a surgical instrument used during the procedure.

2. The system of claim 1, wherein the distance sensors are arranged in a shape selected from the group consisting of a rectangle, a square, a circle, a triangle, and an ellipse.

3. The system of claim 1, wherein a face of the sensor array body is substantially flat, and wherein the at least one processor is contained within the sensor array body.

4. The system of claim 1, wherein the distance sensors comprise a type selected from the group consisting of an optical sensor, an ultrasonic sensor, and a magnetic sensor.

5. The system of claim 1, wherein the at least one processor is configured to determine the three-dimensional location of the plurality of registered points by, for each sensor of the plurality of distance sensors:
   (i) determining an origin position for a probe signal transmitted by that sensor, wherein the origin position indicates that sensor's position within the procedure space, based upon the position and the orientation of the sensor array body, and
   (ii) determining a registered point for that sensor based upon the origin position and a distance traveled by the probe signal before striking the registration point of the target area.

6. The system of claim 5, wherein the at least one processor is further configured to:
   (i) determine an orientation of the target area relative to the sensor array body,
   (ii) where the target area and the sensor array body are not substantially parallel, determine, for each sensor of the plurality of distance sensors, an offset value, and
   (iii) determining the registered point for that sensor based upon the origin position, the distance traveled by the probe signal, and the offset value.

7. The system of claim 6, further comprising a target area orientation sensor configured to provide an orientation of the target area to the at least one processor.

8. The system of claim 1, wherein the distance sensors are configured to be positioned and operable at a distance of between about 4 inches and 20 inches from the target location when the location of the plurality of registered points is determined.

9. The system of claim 1, further comprising an orientation indicator, wherein the orientation indicator is configured to provide an indication to a user when the sensor array body is not substantially parallel to the target area.

10. The system of claim 1, further comprising an automated arm, wherein the automated arm is operable to orient the sensor array body so that it is substantially parallel to the target area.

11. The system of claim 1, wherein the plurality of distance sensors comprises at least 30 individual sensors, and wherein the plurality of distance sensors are positioned on the sensor array body such that the transmitted probe signals strike substantially all of the target area.

12. The system of claim 1, wherein the at least one processor is further configured to, for any sensor of the plurality of distance sensors whose probe signal falls outside of the target area during use, disregard proximity data from that sensor.

13. The system of claim 1, wherein the plurality of distance sensors are configured to be activated once in order to gather the data used to determine the three-dimensional location of the plurality of registered points.

14. A registration probe comprising:
   (a) an elongate body adapted to be held by a user, the elongate body comprising a distal tip;
   (b) a target sensor located at the distal tip, wherein the target sensor is operable to detect the distance to a point on a patient's face in front of the distal tip;
   (c) a position sensor operable to provide a position and an orientation for the registration probe; and
   (d) at least one processor configured to:
      (i) activate the target sensor,
      (ii) determine the three-dimensional location of the point within a procedure space based upon a signal from the target sensor indicating the distance to the point, and the position and orientation of the registration probe at the time the signal is received from the target sensor,
      (iii) add the three-dimensional location of the point to a plurality of registered points that are associated with different points on the patient's face,
      (iv) associate the plurality of registered points with a set of pre-operative images of the patient, and
      (v) provide an image guided surgery navigation interface during a procedure based upon the association of the plurality of registered points and the set of pre-operative images.

15. The registration probe of claim 14, further comprising a proximity trigger configured to cause the target sensor to activate and determine the three-dimensional location of the point when the distal tip is within a configured capture distance of the target.

16. The registration probe of claim 14, wherein the target sensor comprises a capacitive sensor or a resistive sensor.

17. The registration probe of claim 14, wherein the target sensor comprises an optical sensor.

18. The registration probe of claim 14, wherein the position sensor comprises a type selected from the group consisting of an accelerometer based sensor, a magnetic based sensor, and a wireless beacon based sensor.

19. A method for registering facial landmarks for image guided surgery navigation comprising the steps:

(a) positioning a sensor array so that a plurality of distance sensors of the sensor array are directed at and substantially parallel to a target area, wherein the target area is patient's facial area;
(b) activating the sensor array to capture a set of distances indicating the distance traveled by a probe signal originating from each of the plurality of distance sensors before striking a target point within the target area;
(c) determining a position and an orientation of the sensor array within three-dimensional space;
(d) producing a set of registered points by, for each target point within the target area, determining the three-dimensional position of that target point based upon the position and the orientation of the sensor array, and the distance traveled by the probe signal;
(e) creating a navigation data set by associating the set of registered points with a set of pre-operative images; and
(f) providing image guided surgery navigation based upon the navigation data set.

* * * * *

UNITED STATES PATENT AND TRADEMARK OFFICE
CERTIFICATE OF CORRECTION

Page 1 of 1

PATENT NO. : 10,786,311 B2
APPLICATION NO. : 15/852169
DATED : September 29, 2020
INVENTOR(S) : Henry F. Salazar et al.

It is certified that error appears in the above-identified patent and that said Letters Patent is hereby corrected as shown below:

On the Title Page

Inventors item (72), Line 5, reads "...(US); Itzhak Fang, Jr., Irvine, CA..."; which should be deleted and replaced with "...(US); Itzhak Fang, Irvine, CA..."

Signed and Sealed this
Seventeenth Day of November, 2020

Andrei Iancu
*Director of the United States Patent and Trademark Office*